(12) United States Patent
Guffogg et al.

(10) Patent No.: US 7,317,041 B2
(45) Date of Patent: Jan. 8, 2008

(54) METHOD FOR THE PREPARATION OF BILIQUID FOAM COMPOSITIONS

(75) Inventors: Philip Ernest Guffogg, Ponsanooth (GB); Derek Alfred Wheeler, Dorking (GB)

(73) Assignee: Disperse Limited, Guildford, Surrey (GB)

( * ) Notice: Subject to any disclaimer, the term of this patent is extended or adjusted under 35 U.S.C. 154(b) by 348 days.

(21) Appl. No.: 10/503,091

(22) PCT Filed: Jan. 31, 2003

(86) PCT No.: PCT/GB03/00421

§ 371 (c)(1),
(2), (4) Date: Aug. 30, 2004

(87) PCT Pub. No.: WO03/064024

PCT Pub. Date: Aug. 7, 2003

(65) Prior Publication Data

US 2005/0049315 A1 Mar. 3, 2005

(30) Foreign Application Priority Data

Jan. 31, 2002 (GB) ................................. 0202312.5

(51) Int. Cl.
*B01F 3/08* (2006.01)
*B01F 17/00* (2006.01)
*B01J 13/00* (2006.01)

(52) U.S. Cl. .............................. 516/73; 516/9; 516/10; 516/53; 516/72; 516/925

(58) Field of Classification Search .................. 516/10, 516/925, 73, 9, 53, 72
See application file for complete search history.

(56) References Cited

U.S. PATENT DOCUMENTS

| | | | | |
|---|---|---|---|---|
| 3,467,646 A | * | 9/1969 | Perez et al. | 521/122 |
| 3,967,921 A | * | 7/1976 | Haberli et al. | 8/477 |
| 4,486,333 A | | 12/1984 | Sebba | |
| 6,054,319 A | | 4/2000 | Worden et al. | |
| 6,165,479 A | * | 12/2000 | Wheeler | 424/400 |
| 6,312,760 B1 | | 11/2001 | Wheeler | |
| 6,361,802 B1 | | 3/2002 | Schmidt | |
| 2002/0058055 A1 | | 5/2002 | Zecchino et al. | |
| 2003/0148722 A1 | * | 8/2003 | Lombardo et al. | 451/529 |

OTHER PUBLICATIONS

Sebba, F., Biliquid Foams—A Preliminary Report, Journal of Colloid and Interface Science, vol. 40, No. 3, Sep. 1972 pp. 468-474.*
Sebba, F., Foams and Biliquid Foams—Aphrons, John Wiley & Sons, 1987, Ch. 8, pp. 103-127.*

* cited by examiner

*Primary Examiner*—Randy Gulakowski
*Assistant Examiner*—Timothy J. Kugel
(74) *Attorney, Agent, or Firm*—Dykema Gossett PLLC (57) ABSTRACT

A method for the preparation of a biliquid foam which does not rely upon the initial formation of a gas foam, in which a stirrer having a single or a multiplicity of blades is used, the stirrer being operated in a manner such that at least one part of the stirrer mechanism breaks the interface between the continuous polar phase used to form the biliquid foam and the air, the non-polar phase being added dropwise at least initially whilst stirring the continuous polar phase and the rate of addition of the non-polar phase being controlled so that a biliquid foam composition is formed.

12 Claims, 3 Drawing Sheets

METHOD FOR THE PREPARATION OF BILIQUID FOAM COMPOSITIONS

The present invention relates to polyaphron (or biliquid foam) compositions and, in particular, to a novel method for the preparation of such compositions.

Traditionally, biliquid foams have been made using processes that rely upon the initial use of gas foams or upon polyaphrons which themselves have previously been made using gas foams. Reference is made to U.S. Pat. No. 4,486,333 and Sebba, "*Foams and Biliquid Foams, Aphrons*", John Wiley & Sons, 1987, p. 106. The use of gas foams in the manufacture of biliquid foams is a cumbersome manufacturing process which suffers from a number of problems. These are associated with the need to generate the gas, the need to remove the gas, the lack of control of the biliquid foam particle size which results and, when a previously made biliquid foam is used, the question of uniformity of the composition of the biliquid foam being freshly made in comparison to that of the previously made biliquid foam.

Biliquid foams were first described in 1972 by Sebba, F., *J. Coll. and Interface Sci.*, 40, 468 1972. Since then, they have been used to formulate and manufacture a wide range of products, especially in conjunction with the stablising influence of an aqueous polymer gel, for example as described in WO97/32559. The method of manufacture of heterosept (oil-in-water) biliquid foams has followed the process first described by Sebba in 1972. This method comprises forming a gas foam on the surface of an aqueous, surfactant-containing medium (which will eventually form the external phase of the biliquid foam) to which a surfactant-containing oil phase is added slowly, drop wise and with stirring to form a number of new polyaphron droplets. As the number of new particles increases, the rate of addition of the oil phase can be increased as the new particles provide an increased surface area on which to form new polyaphrons.

An alternative method was described by Sebba, which is based upon the principle of 'seeding'. In this process, a quantity (unspecified) of previously made biliquid foam is added to the aqueous phase prior to the 'new' oil phase being added. In this way, the existing polyaphron droplets form a large surface for new droplet formation as an alternative to the previously described gas foam.

Sebba also describes a mechanical device for producing biliquid foams in Sebba, '*Foams and Biliquid Foams, Aphrons*', John Wiley & Sons, 1987 pp 110-111, which comprises a cylindrical tube positioned horizontally on a stand. Centered along the tube there is a rotating shaft to which four Plexiglass blades are attached with distal ends that just clear the tube. There are provided four entry points along the tube that allow the introduction of the two phases. The first provides an entry for the aqueous phase and the other three the oil phase. The ratio of feed rates for each of the entry point needs to be closely controlled. In use, the shaft is caused to rotate at about 1000 rpm. A slight tilt is imposed on the tube such that the contents flow towards an exit point at the lower end of the tube. For start up the tube is primed with polyaphrons that are prepared by use of a gas foam. Sebba also describes a method for producing small amounts of polyaphrons by shaking an aqueous solution of a surfactant to produce a gas foam in a bottle or similar container, and then adding the oil phase thereto dropwise with intermediate shaking.

All of the methods described above are problematical for the production of biliquid foams for a number of reasons.

First, the use of a gas foam to provide the initial basis for the production of biliquid foams does not easily lend itself to the large-scale production of polyaphrons which may be used to manufacture cosmetic or pharmaceutical products. The formation of gas foams is unusual and is practically unknown in many industries that might be expected to benefit from the large-scale use of biliquid foams.

Secondly, the inclusion of gas in many product types utilising polyaphrons is unacceptable on the grounds of introducing instability (for example, oxidation) or interfering with the ability to pack or fill known quantities of the product, since the inclusion of gas will reduce the bulk density of the product.

In the event that a 'seeding' process is used (as described above) the problem encountered is that the material used for seeding will be a different batch to that being manufactured. In some industries (notably cosmetics and pharmaceuticals) the mixing of batches in this way is unacceptable. Moreover, if the seeding material is not identical in composition to the batch being made, then discrepancies in the formula will arise and this, again is unacceptable.

The device illustrated and described by Sebba for the continuous manufacture of biliquid foams is cumbersome, fragile and not suitable for full-scale production. Moreover, it suffers from the problem discussed above with respect to seeding.

Accordingly, no suitable, efficient method for the full-scale production of biliquid forms is provided by the prior art.

The present invention provides a method for the large-scale production of biliquid foams that does not suffer from any of the deficiencies noted above. In particular, it utilises production equipment that is well known and commonly used in most, if not all of the industries likely to make use of polyaphrons. It does not rely upon the production of gas foams, or previously manufactured batches of biliquid foams.

It has surprisingly been discovered that biliquid foams can be made by a stirring method provided that a stirrer is used with a multiplicity of blades at least one of which is positioned to cut the air/liquid surface of the aqueous phase of the batch before the addition of the oil and provided that the addition of the oil phase to the aqueous phase is carefully controlled.

Accordingly, the present invention provides a method for the preparation of a biliquid foam composition which method comprises the steps of:

i) introducing into a mixing vessel equipped with a stirrer having a single or a multiplicity of stirrer blades, a continuous polar phase which optionally contains a surfactant for the preparation of the biliquid foam, the stirrer operating in a manner such that at least one part of the stirrer mechanism breaks the interface between the continuous polar phase and the air;

ii) stirring the continuous polar phase;

iii) adding a non-polar phase which optionally contains a surfactant for the preparation of the biliquid foam at least initially at a controlled rate to the continuous polar phase whilst continuing stirring, the rate of addition of the non-polar phase being controlled so that the droplets of the non-polar phase which lie on the surface of the continuous polar phase are broken up into smaller droplets by the action of the stirrer blade breaking the interface between the continuous polar phase and the non-polar phase; it being understood that a surfactant has to be included m at least one of the polar or non-polar phases; and iv) thereby forming a plurality of biliquid foam particles comprising non-polar phase droplets encapsulated in a film of the continuous polar phase, which particles act as nucleating sites providing additional surfaces for the preparation of the biliquid foam.

As detailed above, the main advantage of the method of the present invention is that the biliquid foams can be prepared without the requirement to first form a gas foam, or to use a seeding method in which the seeds have been prepared using a gas foam.

A second advantage is that using the method of the present invention the addition of a second surfactant is not always required, thus reducing the complexity, cost and skin-irritation potential of the resulting biliquid foam.

In carrying out the method of the present invention the addition of the non-polar phase in step (iii) of the method is preferably an initial dropwise addition. The rate of addition may be increased when sufficient nucleating sites have been formed to prevent the break-up of the biliquid foam which is being formed, or the formation of an oil in water in oil (o/w/o) system.

During the preparation of the biliquid foams of the present invention it is preferred that the stirrer is operated in such a manner that the whole volume of the liquid is stirred during steps (i), (ii) and (iii) of the preparation of the biliquid foam.

The non-polar phase which may be used in the biliquid foam will in general be liquid at room temperature and may be, for example, a cyclomethicone, dimethicone, phenyl trimethicone, dimethiconol, dimethicone copolyol, trimethylsiloxysilicate, an emollient ester such as isopropyl isostearate, lanolate, myristate or palmitate, or octyl palmitate, a glyceride such as avocado oil, coconut oil, soybean oil or sunflower oil, or a caprylic/capric triglyceride, a lanolin oil, mineral oil or natural oil, or oleyl alcohol, or a petroleum derivative, such as diesel, gasoline or kerosene, or mixtures of the foregoing.

The polar liquid forms the continuous phase in the biliquid foams and is preferably water, in particular deionized water. The polar liquid may alternatively comprise water in admixture with another polar liquid, for example a $C_1$-$C_3$ alcohol, a $C_4$ alcohol containing at least two hydroxy groups or ethylene glycol, or mixtures thereof. When the non-polar phase is a petroleum derivative, the polar phase will generally comprise from 50% to 99% of the $C_1$-$C_4$ alcohol or ethylene glycol, or mixtures thereof.

The surfactant used at a low level in the present invention may be incorporated into the polar or non-polar phase, or both phases, and may be, for example:— a cationic surfactant such as an amidoamine, a quaternary ammonium compound or a sulphonium salt;

an amphoteric surfactant such as an acylaminoacid, an N-substituted alkylamine, an N-alkyl-β-aminopropionate, an N-alkylbetaine, an alkylimidazoline or a sulphobetaine;

an anionic surfactant such as an acyl-lactate, N-acylsarcosinate, alkyl-carboxylate (either mono- or polyvalent), alkyl ether carboxylate, N-alkyl-glutamate, fatty acid-peptide condensate, phosphated ethoxylated alcohol, alkyl sulphate, ethoxylated alkyl sulphate, alpha-olefin sulphonate or ester-linked sulphonate;

a nonionic surfactant such as an alkanolamide, amine oxide, ester of a polyhydric (for example an ester of an ethylene, diethylene or propylene glycol, or glycerol or a polyglycerol, or sorbitan, glucose or sucrose), a polyoxyethylene or polyoxypropylene derivative of an alcohol, amide or ester, or a polyoxyethylene/polyoxypropylene block copolymer;

or a suitable compatible mixture of these surfactants.

The surfactant will generally be included primarily in either the polar phase or non-polar phase in an amount of from 0.01% to 3% by weight, preferably in an amount of from 0.1% to 1.0% by weight based on the total weight of the formulation.

It will be understood by those skilled in the art that the choice of surfactant will also depend upon the particular non-polar liquid and the particular polar liquid and the amount thereof which are used in the preparation of the biliquid foams.

The surfactant which is used in the present invention may also be used in combination with a co-surfactant, such as a polyoxyethylene oleyl ether, a polyoxyethylene lauryl ether, a polyisobutylene succinimide ester, polyiso-butylene succinimide amine or Mannich base.

The biliquid foam compositions of the present invention may also contain other additives such as preservatives (for instance to prevent microbiological spoilage) or corrosion inhibitors. These additives may be included in the non-polar liquid or the continuous phase.

It will be understood that the inclusion of these additives will be at the levels and with the type of materials which are found to be effective and useful.

The method of the present invention is carried out using a mixing vessel equipped with a stirrer preferably having a multiplicity of stirrer blades that stir the whole volume. Examples of stirrers which may be used in the present invention include a flat blade impeller, a Rushton impeller or a radial flow impeller having a plurality of impellers arranged vertically on a shaft, an orbital mixer or a stirrer comprising a main rotating blade and an inter-digitating counter-rotating blade.

The characteristics of the biliquid foam are dependant on the shear applied during manufacture. The shear itself is dependent upon the ratio of the impeller diameter to vessel diameter and the speed of rotation of the impeller. The ratio of the impeller diameter to vessel diameter will preferably be at least 0.8. For an impeller to vessel diameter ratio of 0.8 to 0.9 a useful standard impeller speed can be calculated from equation 1 below. A higher speed will reduce the particle size and enhance the plastic/shear thinning nature of the rheology while a lower speed will produce the opposite effect.

$$\omega = \frac{5.8 \times 10^{-1}}{r} \text{radsec}^{-1} \qquad \text{Equation 1}$$

where
  ω)=angular velocity/rad.sec$^1$
  r=impeller radius/m

The ratio or impeller to vessel diameter can be reduced below 0.8 with a concomitant increase in the product particle size. To overcome this, an increased impeller speed can be used bearing in mind the minimum usable impeller to vessel ratio is limited to the region where localised flow predominates at useable shear rates, usually at an impeller to vessel diameter ratio of 0.4 to 0.5, when conditions to maintain full flow will dramatically alter the properties of the biliquid foam thereby reducing the controllability of the process. Typical impeller speeds used in the production of biliquid foams in accordance with the present invention are from 5 to 400 rpm, ranging from a typical industrial to a small laboratory scale.

The processing procedure is largely independent of the mixing geometry employed. The vessel is charged with the aqueous phase and agitation is begun. The oil is added towards the outside of the vessel close to the point of maximum agitation by the edge of the impeller at a rate that is dependent primarily upon the physiochemical nature of the formulation. The maximum rate of addition is limited by the necessity to avoid two undesirable conditions. The first is an inversion of the formulation characterised by the formation of a water in oil (w/o) system. The second is the occurrence of the situation whereby the uptake of oil into the body of the forming biliquid foam is lower than the oil addition rate. This can lead to a situation in which the biliqud foam breaks up and becomes dispersed within the oil to form an oil in water in oil (o/w/o) system.

On completion of the oil phase addition, the stirring is continued until the particle size has stabilised. This process typically takes 20 min under the ideal processing parameters mentioned previously.

An enhanced oil addition rate may be achieved by the use of multiple points of oil addition to the formulation. This will result in a reduction of the maximum local concentration of oil for a given addition rate that otherwise, in the case of single point oil addition, may create conditions that would lead to the two previously mentioned undesirable conditions. The limit to the extent of this procedure will be the situation whereby two or more of the oil addition points interact to create a local concentration great enough for the formation of an o/w/o or w/o system.

The present invention will be further described with reference to the accompanying drawings in which.

Figure 1A:
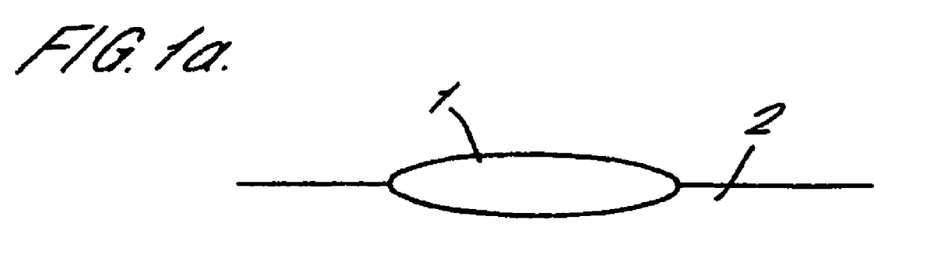
FIGS. 1a, b and c illustrate schematically the way in which biliquid foams are formed using the method of the invention.
Figure 1B:
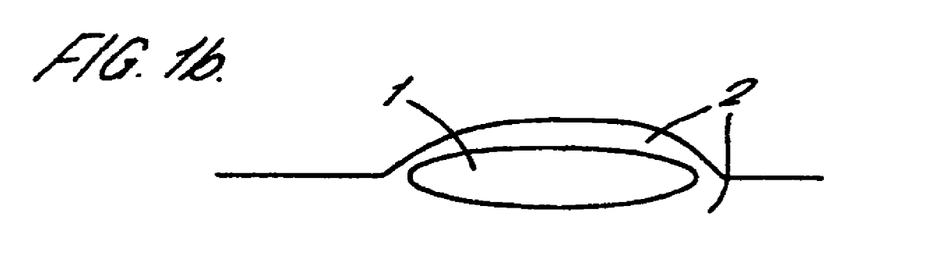
Figure 1C:
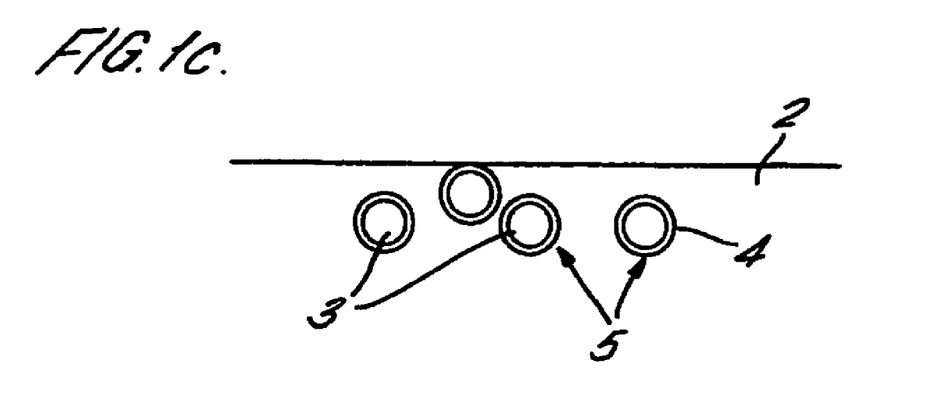

Referring to the drawings, the way in which the biliquid foams are formed using the method of the present invention is shown stepwise in FIGS. 1a, 1b and 1c. In FIG. 1a a droplet of oil 1 is shown, without mixing, lying on the surface of the aqueous phase 2 in the form of a thin lens. As the surface of the aqueous phase is agitated in the method of the present invention as the stirrer breaks the interface between the aqueous phase and air, this results simultaneously in a thin layer of water spreading over the upper surface of the oil lens 1 as shown in FIG. 1b and the break up the oil droplet 1 into a plurality of smaller oil droplets 3 which are surrounded by an encapsulating, aqueous soap film 4 as shown in FIG. 1c. These small droplets 3 encapsulated with an aqueous soap film 4 are biliquid foam particles or polyaphrons 5. Once these few initial polyaphrons 5 have been produced, they in turn provide additional surfaces for the further formation of more polyaphrons.

Figure 2:
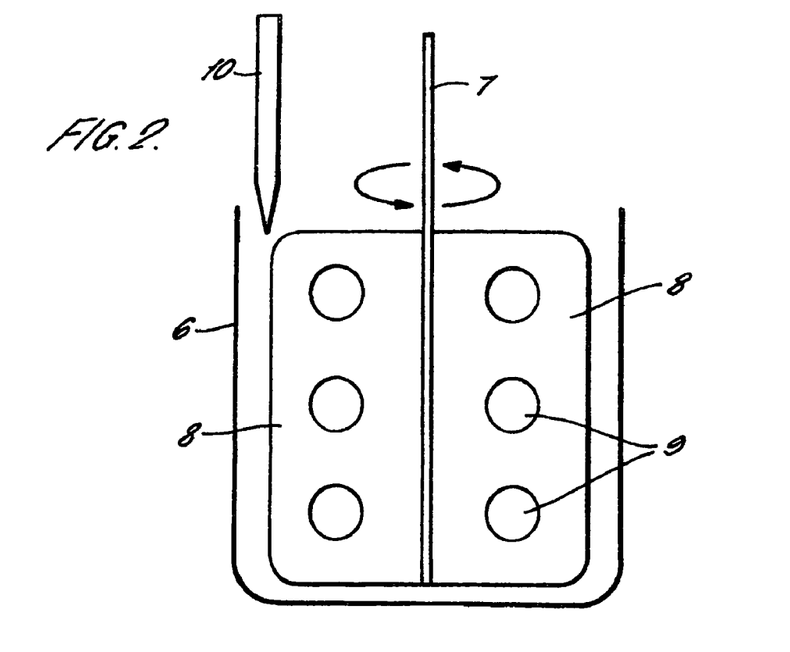
FIG. 2 illustrates schematically a simple apparatus for the production of biliquid foams.

Referring to FIG. 2, a simple small scale production apparatus is illustrated. A beaker 6 is provided which incorporates therein an impeller which comprises a vertical shaft 7 to which there is attached a flat blade impeller 8. The impeller blade 8 is provided with a plurality of holes 9 which assist in the mixing of the liquids in the vessel 6. The shaft of the impeller 7 is attached to a variable speed motor (not shown). An oil introduction nozzle 10 is shown for the introduction of oil into the vessel 6. The oil is added dropwise at least initially during the manufacture of the biliquid foam.

Figure 3:
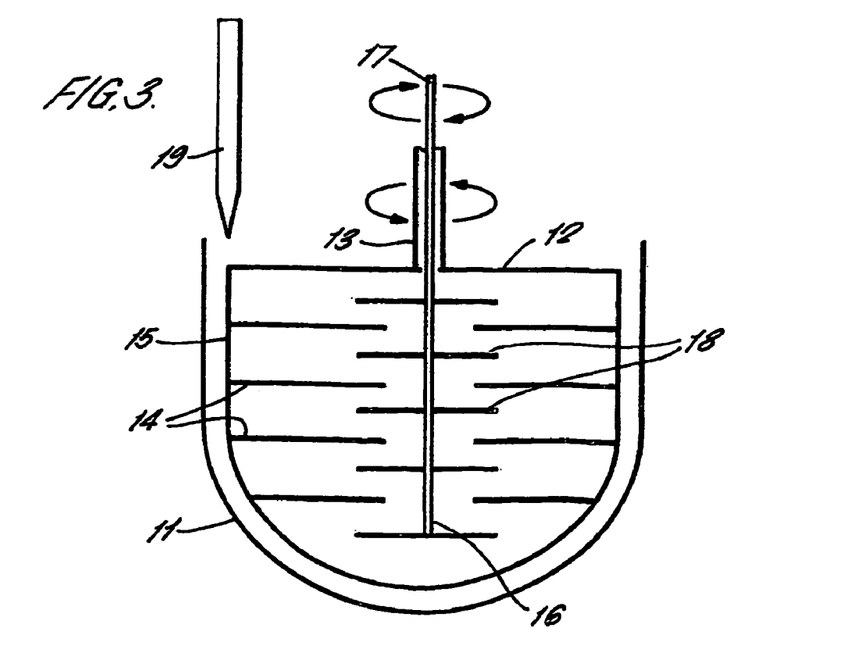
FIG. 3 illustrates schematically a more complex mixing apparatus.

FIG. 3 illustrates a more advanced mixing apparatus of the type that is typically used in the manufacture of cosmetics. A manufacturing vessel 11 is equipped with a main rotating paddle 12 which rotates around a hollow shaft 13. The rotating paddle 12 has a plurality of blades 14 which are attached to the outside frame 15 of the paddle. An interdigitating counter-rotating paddle 16 is attached to a shaft 17 which extends through the hollow shaft 13 of the rotating paddle 12. The paddle 16 has a plurality of blades 18 which extend horizontally between the blades 14 of the rotating paddle 12. An oil introduction nozzle 19 is shown for the introduction of the oil into the vessel 11.

An apparatus as illustrated in FIG. 3 usually possesses a localised high shear mixing capability at the bottom of the vessel. This is not required for the actual production of the biliquid foam, but may be used to reduce the biliquid foam particle size when unusually low particle sizes are required.

The main criteria for selecting a suitable mixing geometry are detailed below.

Biliquid foams exhibit a non-Newtonian (high low shear viscosity and shear thinning) rheology that fits the Cross model detailed in equation 1 and becomes more pronounced as the particle size decreases, or the internal phase volume fraction increases.

$$\frac{\eta - \eta_\infty}{\eta_o - \eta_\infty} = \frac{1}{1 + (K\gamma)^m} Pas \qquad \text{Equation 2}$$

where
$\eta$=viscosity/Pa·s
$\eta_o$ limiting low shear viscosity/Pa·s (8.322)
$\eta_{28}$ limiting high shear viscosity/Pa·s (0.05579)
K=sample constant/s (0.9238)
m=material power low index (0.8449)
$\gamma$=shear rate/s The numerical values in brackets relate to the parameters when applied to Example 1.

Figure 4:
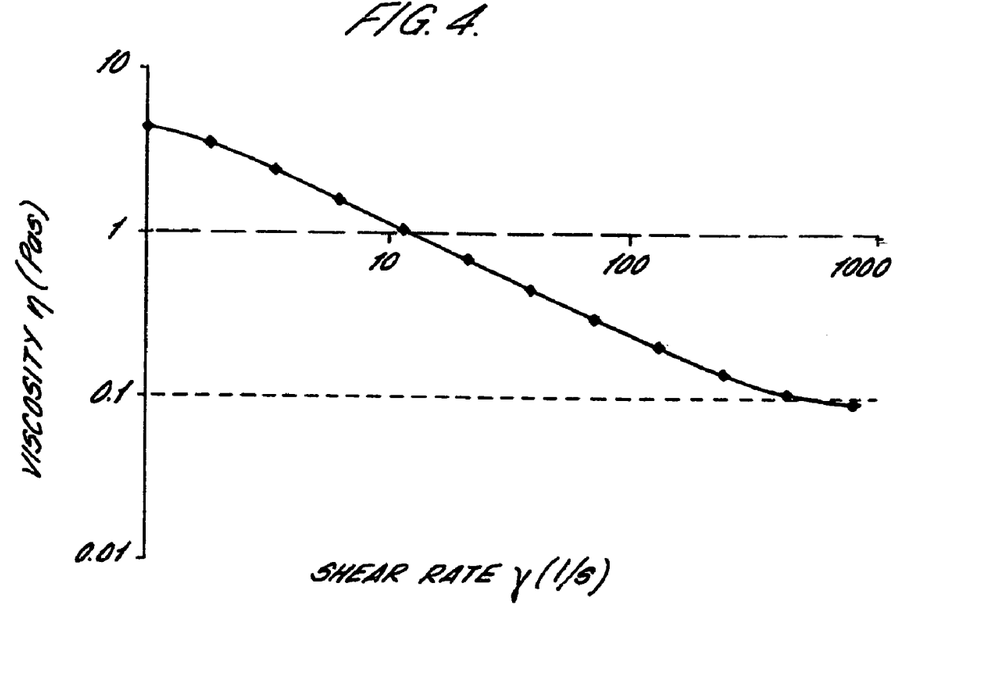
FIG. 4 is a graph illustrating the viscosity profile of the biliquid foam prepared according to Example 1.

This is illustrated in FIG. 4 which is a graph illustrating the biliquid foam viscosity profile of the biliquid foam prepared according to Example 1

Figure 5:
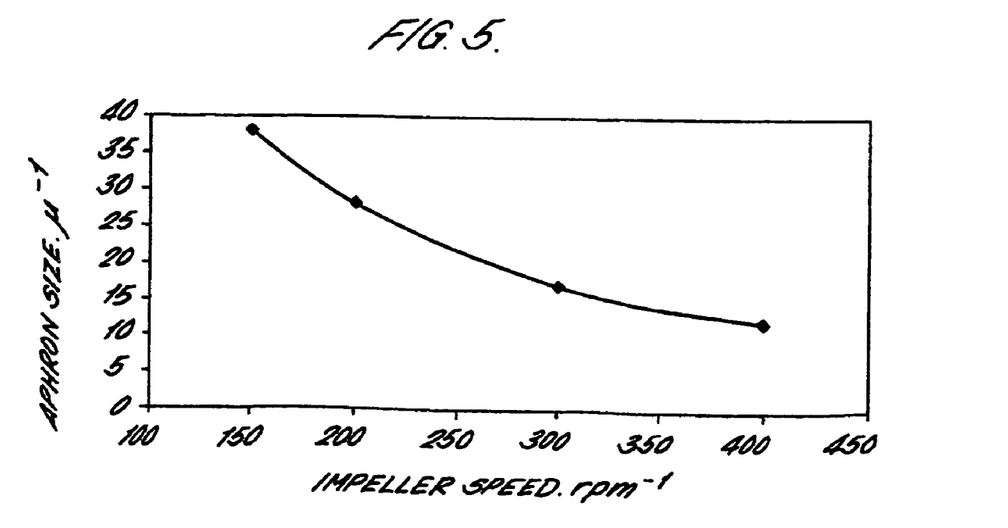
FIG. 5 illustrates the effect of impeller speed on the biliquid foam particle size of the biliquid foam prepared according to Example 1.

It is this behaviour that should be considered when deciding what apparatus is suitable for the manufacturing process. As with all fluids that possess these properties, when mixed by an impeller, the velocity or flow of the biliquid foam will decrease rapidly with the distance from the impeller restricting useful flow to a "cavern" of liquid around the impeller. The particle size, shown in FIG. 5, for the biliquid foam prepared according to the procedure of Example 1 using different impeller speeds for the homogenisation, of the product, and hence the properties of the biliquid foam will be dependent upon the shear that has been applied during manufacture, requiring the same conditions to be applied to the whole volume of the product to produce a homogenous product. If the input of the mixing energy is restricted to a localised region, it will require a high input of energy at this point to give sufficient flow to provide complete mixing of the whole product within the mixing vessel. This high shear input will result in a reduction of the biliqiud foam particle size and an increase in the shear thinning/plastic rheology behavior that will further reduce the size of the flow "cavern" and exacerbate the situation with a resulting loss of control of the process. The input of mixing energy should therefore ideally be applied to the whole body of the biliquid foam or else if it is localised to a small region of the vessel then auxiliary low shear agitation will be required to circulate the whole volume of the biliquid foam through this region to obtain a homogenous product. This secondary mixing will necessarily be of a lower shear rate than the localised mixing, or the localised mixing will become redundant and unnecessary.

The present invention will be further described with reference to the following Examples.

EXAMPLE 1

|  | % w/w |
|---|---|
| Oil Phase | |
| Mineral Oil | 89.10 |
| $C_{12-13}$ Pareth-3 | 0.90 |
| Aqueous Phase | |
| Demin. Water | 9.80 |
| Sodium Lauryl ether sulphate (2EO) | 0.10 |
| Preservative | 0.10 |

Sample size 30 g

Preparation

The aqueous phase was premixed until homogenous and placed in a 250 ml squat beaker of internal diameter 67 mm. A 4 blade axial flow impeller of diameter 55 mm was lowered into the beaker to agitate the aqueous phase, ensuring that the impeller cut the air/liquid interface, and rotated at 200 r.p.m. A single point oil addition was used and the oil phase was added initially dropwise at a rate of 5.4 g·min$^{-1}$. The oil addition rate was increased to 24.3 g·min$^{-1}$ after 30 seconds and continued at that rate for a further 1 minute. Agitation was continued for a further 20 minutes in order to homogenise the product.

Sample size distribution in micrometres

| d(0.1) | 17.96 |
|---|---|
| d(0.5) | 26.07 |
| d(0.9) | 37.30 |

EXAMPLE 2

|  | % w/w |
|---|---|
| Oil Phase | |
| Diesel fuel | 80.00 |
| Aqueous Phase | |
| Ethanol | 13.3 |
| Demin. Water | 5.7 |
| Croduret 50 | 1.00 |

Sample size 50 g

Preparation

The aqueous phase was premixed until homogenous and placed in a 250 ml squat beaker of internal diameter 67 mm. A 4-blade axial flow impeller of diameter 55 mm was lowered into the beaker to agitate the aqueous phase, ensuring that the impeller cut the air/liquid interface, and rotated at 200 r.p.m. A single point oil addition was used and the oil phase was added initially dropwise at a rate of 0.8 g·min$^{-1}$ The oil addition rate was increased to 2.4 g·min$^{-1}$ after 5 minutes and continued at that rate for a further 15 minutes. Agitation was continued for a further 20 minutes in order to homogenise the product.

Sample size distribution in micrometres

| d(0.1) | 8.79 |
|---|---|
| d(0.5) | 13.60 |
| d(0.9) | 20.99 |

EXAMPLE 3

|  | % w/w |
|---|---|
| Oil Phase | |
| Diesel fuel | 80.00 |
| Aqueous Phase | |
| Ethanol | 13.3 |
| Demin. Water | 5.7 |
| Croduret 50 | 1.00 |

Sample size 1500 g

Preparation

The aqueous phase was premixed until homogenous and placed in a 2.0 l squat beaker of internal diameter 123 mm. A flat blade impeller of diameter 100 mm was lowered into the beaker to agitate the aqueous phase, ensuring that the impeller cut the air/liquid interface, and rotated at 110 r.p.m. A single point oil addition was used and the oil phase was added dropwise initially at a rate of 10.08 g·min$^{-1}$. The oil addition rate was increased to 76.64 g·min$^{-1}$ after 5 minutes and continued at that rate for a further 15 minutes. Agitation was continued for a further 20 minutes in order to homogenise the product.

Sample size distribution in micrometres

| d(0.1) | 10.33 |
|---|---|
| d(0.5) | 18.75 |
| d(0.9) | 32.78 |

EXAMPLE 4

|  | % w/w |
|---|---|
| Oil Phase | |
| Diesel fuel | 80.00 |
| Polar Phase | |
| Methanol/water (96%/4% mixture) | 19.00 |
| Croduret 50 | 1.00 |

Sample size 50 g

Preparation

The polar phase was premixed until homogenous and placed in a 250 ml squat beaker of internal diameter 67 mm. A 4-blade axial flow impeller of diameter 55 mm was lowered into the beaker to agitate the aqueous phase, ensuring that the impeller cut the air/liquid interface, and rotated at 200 r.p.m. A single point oil addition was used and the oil phase was added dropwise initially at a rate of 0.8 g·min$^{-1}$. The oil addition rate was increased to 2.4 g·min$^{-1}$ after 5 minutes and continued at that rate for a further 15 minutes. Agitation was continued for a further 20 minutes in order to homogenise the product.

Sample size distribution in micrometres

| | |
|---|---|
| d(0.1) | 16.67 |
| d(0.5) | 28.55 |
| d(0.9) | 47.42 |

EXAMPLE 5

| | % w/w |
|---|---|
| Oil Phase | |
| Diesel fuel | 80.00 |
| Aqueous Phase | |
| Ethylene glycol | 17.10 |
| Demin. Water | 1.90 |
| Croduret 50 | 1.00 |

Sample size 50 g

Preparation

The aqueous phase was premixed until homogenous and placed in a 250 ml squat beaker of internal diameter 67 mm. A 4-blade axial flow impeller of diameter 55 mm was lowered into the beaker to agitate the aqueous phase, ensuring that the impeller cut the air/liquid interface, and rotated at 200 r.p.m. A single point oil addition was used and the oil phase was added initially dropwise at a rate of 0.8 g·min$^{-1}$ The oil addition rate was increased to 2.4 g·min$^{-1}$ after 5 minutes and continued at the rate for a further 15 minutes. Agitation was continued for a further 20 minutes in order to homogenise the product.

Sample size distribution in micrometers

| | |
|---|---|
| d(0.1) | 8.79 |
| d(0.5) | 13.60 |
| d(0.9) | 20.99 |

EXAMPLE 6

| | % w/w |
|---|---|
| Oil Phase | |
| Finalan 75 (Kerosene) | 80.00 |
| Aqueous Phase | |
| Ethylene glycol | 13.30 |
| Demin. Water | 5.70 |
| Croduret 50 | 1.00 |

Sample size 50 g

Preparation

The aqueous phase was premixed until homogenous and placed in a 250 ml squat beaker of internal diameter 67 mm. A 4 blade axial flow impeller of diameter 55 mm was lowered into the beaker to agitate the aqueous phase, ensuring that the impeller cut the air/liquid interface, and rotated at 200 r.p.m. A single point oil addition was used and the oil phase was added dropwise initially at a rate of 0.8 g·min$^{-1}$. The oil addition rate was increased to 2.4 g·min$^{-1}$ after 5 minutes and continued at that rate for a further 15 minutes. Agitation was continued for a further 20 minutes in order to homogenise the product.

Sample size distribution in micrometres

| | |
|---|---|
| d(0.1) | 8.43 |
| d(0.5) | 13.73 |
| d(0.9) | 22.29 |

EXAMPLE 7

| | % w/w |
|---|---|
| Oil Phase | |
| Dimethicone 100 cps | 89.10 |
| C$_{12-13}$ Pareth-3 | 0.90 |
| Aqueous Phase | |
| Demin. Water | 9.80 |
| Sodium Lauryl ether sulphate (2EO) | 0.10 |
| Preservative | 0.10 |

Sample size 30 g

Preparation

The aqueous phase was premixed until homogenous and placed in a 250 ml squat beaker of internal diameter 67 mm. A 4-blade axial flow impeller of diameter 55 mm was lowered into the beaker to agitate the aqueous phase, ensuring that the impeller cut the air/liquid interface, and rotated at 200 r.p.m. A single point oil addition was used and the oil phase was added dropwise at a rate of 13.5 g·min$^{-1}$ over 2 minutes. Agitation was continued for a further 20 minutes in order to homogenise the product.

Sample size distribution in micrometres

| | |
|---|---|
| d(0.1) | 5.16 |
| d(0.5) | 9.15 |
| d(0.9) | 14.81 |

EXAMPLE 8

| | % w/w |
|---|---|
| Oil Phase | |
| Capric/caprylic Triglyceride | 89.10 |
| C$_{12-13}$ Pareth-3 | 0.90 |
| Aqueous Phase | |
| Demin. Water | 9.80 |
| Sodium Lauryl ether sulphate (2EO) | 0.10 |
| Preservative | 0.10 |

Sample size 30 g

Preparation

The aqueous phase was premixed until homogenous and placed in a 250 ml squat beaker of internal diameter 67 mm. A 4-blade axial flow impeller of diameter 55 mm was lowered into the beaker to agitate the aqueous phase, ensuring the impeller cut the air/liquid interface, and rotated at 200 r.p.m. A single point oil addition was used and the oil phase was added dropwise at a rate of 5.4 g·min$^{-1}$ over 5 minutes. Agitation was continued for a further 20 minutes in order to homogenise the product.

Sample size distribution in micrometres

| | |
|---|---|
| d(0.1) | 59.31 |
| d(0.5) | 84.38 |
| d(0.9) | 119.76 |

EXAMPLE 9

| | % w/w |
|---|---|
| Oil Phase | |
| Fragrance | 89.10 |
| Oleth-10 | 0.45 |
| Etocas 25 | 0.45 |
| Aqueous Phase | |
| Demin. Water | 9.80 |
| Polysorbate 20 | 0.10 |
| Preservative | 0.10 |

Sample size 30 g

Preparation

The aqueous phase was premixed until homogenous and placed in a 250 ml squat beaker of internal diameter 67 mm. A 4-blade axial flow impeller of diameter 55 mm was lowered into the beaker to agitate the aqueous phase, ensuring that the impeller cut the air/liquid interface, and rotated at 200 r.p.m. A single point oil addition was used and the oil phase was added dropwise at a rate of 2.7 g·min$^{-1}$ over 10 minutes. Agitation was continued for a further 15 minutes in order to homogenise the product.

Sample size distribution in micrometres

| | |
|---|---|
| d(0.1) | 5.65 |
| d(0.5) | 10.60 |
| d(0.9) | 19.15 |

EXAMPLE 10

| | % w/w |
|---|---|
| Oil Phase | |
| Mineral Oil | 90.00 |
| C$_{12-13}$ Pareth-3 | 1.00 |
| Aqueous Phase | |
| Demin. Water | 9.9 |
| Preservative | 0.10 |

Sample size 30 g

Preparation

The aqueous phase was premixed until homogenous and placed in a 250 ml squat beaker of internal diameter 67 mm. A 4 blade axial flow impeller of diameter 55 mm was lowered into the beaker to agitate the aqueous phase, ensuring that the impeller cut the air/liquid interface, and rotated at 200 r.p.m. A single point oil addition was used and the oil phase was added dropwise at a rate of 9.0 g19 min$^{-1}$ over 3 minutes. Agitation was continued for a further 20 minutes in order to homogenise the product.

Sample size distribution in micrometres

| | |
|---|---|
| d(0.1) | 16.17 |
| d(0.5) | 23.50 |
| d(0.9) | 33.84 |

Croduret 50 is a Trade Name for a hydrogenated castor oil/polyethylene glycol adduct available from Croda Chemicals Limited where the suffix 50 refers to the number of ethylene oxide groups in the polyethylene oxide chain.

Etocas 25 is a Trade Name for a castor oil/polyethylene glycol adduct available from Croda Chemicals Limited where the suffix 25 refers to the number of ethylene oxide groups in the polyethylene oxide chain.

The invention claimed is:

1. A method for the preparation of a biliquid foam composition without formation of a gas foam, which method comprises the steps of:
    i) introducing into a mixing vessel equipped with a stirrer having a single or a multiplicity of stirrer blades, a continuous polar phase which optionally contains a surfactant for the preparation of the biliquid foam, the stirrer operating in a manner such that at least one part of the stirrer mechanism breaks the interface between the continuous polar phase and the air;
    ii) stirring the continuous polar phase;
    iii) adding a non-polar phase which optionally contains a surfactant for the preparation of the biliquid foam at least initially at a controlled rate to the continuous polar phase whilst continuing stirring, the rate of addition of the non-polar phase being controlled so that the droplets of the non-polar phase which lie on the surface of the continuous polar phase are broken up into smaller droplets by the action of the stirrer blade breaking the interface between the continuous polar phase and the non-polar phase; a slurfactant being included in at least one of the polar or non-polar phases; and
    iv) thereby forming a plurality of biliquid foam particles comprising non-polar phase droplets encapsulated in a film of the continuous polar phase, which particles act as nucleating sites providing additional surfaces for the preparation of the biliquid foam.

2. A method as claimed in claim 1 wherein the non-polar phase comprises from 60% to 90% by weight of the biliquid foam.

3. A method as claimed in claim 2 wherein the non-polar phase comprises from 75% to 85% by weight of the biliquid foam.

4. A method as claimed in claim 1 wherein the polar continuous phase is aqueous.

5. A method as claimed in claim 1 wherein the stirrer is a flat blade impeller, a Rushton impeller or a radical flow impeller having a plurality of impellers arranged vertically on a shaft.

6. A method as claimed in claim 1 wherein the stirrer is an orbital mixer.

7. A method as claimed in claim 1 wherein the stirrer comprises a main rotating blade and an interdigitating counter-rotating blade.

8. A method as claimed in claim 1 wherein the ratio of the diameter of the stirrer to the diameter of the mixing vessel is at least 0.8.

9. A method as claimed in claim 1 wherein the speed of rotation of the mixer is in the range of from 5 to 400 rpm.

10. A method as claimed in claim 1 wherein the non-polar phase comprises a cyclomethicone, dimethicone, phenyl trimethicone, dimethiconol, dimethicone copolyol, trimethylsiloxysilicate, an emollient ester such as isopropyl isostearate, lanolate, myristate or palmitate, or octyl palmitate, a glyceride such as avocado oil, coconut oil, soybean oil or sunflower oil, or a caprylic/capric triglyceride, a lanolin oil, mineral oil or natural oil, or oleyl alcohol, or a petroleum derivative, such as diesel, gasoline or kerosene, or mixtures thereof.

11. A method as claimed in claim 1 wherein the addition of the non-polar phase in step (iii) of the method is initially a dropwise addition.

12. A method as claimed in claim 1 wherein the stirrer is operated in such a manner that the whole volume of the liquid is stirred during steps (i), (ii) and (iii) of the preparation of the biliquid foam.

* * * * *